US011912689B2

(12) United States Patent
Padmanabhan et al.

(10) Patent No.: US 11,912,689 B2
(45) Date of Patent: Feb. 27, 2024

(54) METHOD FOR ISOLATION OF AN AROMATIC DIANHYDRIDE AND AROMATIC DIANHYDRIDES PREPARED BY THE METHOD

(71) Applicant: SHPP Global Technologies B.V., Bergen op Zoom (NL)

(72) Inventors: Simon Padmanabhan, Mt. Vernon, IN (US); Sivakumar Periyasamy, Bangalore (IN); Gregory L. Hemmer, Mt. Vernon, IN (US); Robert John Werling, Mt. Vernon, IN (US); Ravi Gautam, Bangalore (IN)

(73) Assignee: SHPP GLOBAL TECHNOLOGIES B.V., Bergen op Zoom (NL)

( * ) Notice: Subject to any disclaimer, the term of this patent is extended or adjusted under 35 U.S.C. 154(b) by 379 days.

(21) Appl. No.: 17/251,035

(22) PCT Filed: Jun. 14, 2019

(86) PCT No.: PCT/US2019/037182
§ 371 (c)(1),
(2) Date: Dec. 10, 2020

(87) PCT Pub. No.: WO2019/245898
PCT Pub. Date: Dec. 26, 2019

(65) Prior Publication Data
US 2021/0179593 A1  Jun. 17, 2021

(30) Foreign Application Priority Data
Jun. 18, 2018 (EP) ..................... 18178321

(51) Int. Cl.
C07D 405/12  (2006.01)
C07D 307/89  (2006.01)

(52) U.S. Cl.
CPC ......... C07D 405/12 (2013.01); C07D 307/89 (2013.01)

(58) Field of Classification Search
CPC ........................... C07D 405/12; C07D 307/89
USPC ....................................... 548/454
See application file for complete search history.

(56) References Cited

U.S. PATENT DOCUMENTS

| | | |
|---|---|---|
| 3,389,970 A | 6/1968 | Scheibel |
| 3,875,116 A | 4/1975 | Heath et al. |
| 3,956,320 A | 5/1976 | Heath et al. |
| 4,020,089 A | 4/1977 | Markezich |
| 4,116,980 A | 9/1978 | Webb |
| 4,217,281 A | 8/1980 | Markezich et al. |
| 4,257,953 A | 3/1981 | Williams, III et al. |
| 4,318,857 A | 3/1982 | Webb et al. |
| 4,329,291 A | 5/1982 | Webb et al. |
| 4,329,292 A | 5/1982 | Webb |
| 4,329,496 A | 5/1982 | Webb |
| 4,340,545 A | 7/1982 | Webb et al. |
| 4,417,044 A | 11/1983 | Parekh |
| 4,520,204 A | 5/1985 | Evans |
| 4,571,425 A | 2/1986 | Silva |
| 4,584,388 A | 4/1986 | Webb |
| 4,902,809 A | 2/1990 | Groeneweg et al. |
| 5,359,084 A | 10/1994 | Dellacoletta et al. |
| 6,008,374 A | 12/1999 | Dellacoletta et al. |
| 6,235,866 B1 | 5/2001 | Khouri et al. |
| 6,265,521 B1 | 7/2001 | Fyvie et al. |
| 6,498,224 B1 | 12/2002 | Odle et al. |
| 7,153,394 B2 | 12/2006 | Guggenheim et al. |
| 10,407,397 B2 | 9/2019 | Royer et al. |
| 2006/0205958 A1 | 9/2006 | Brunelle et al. |
| 2009/0056793 A1 | 3/2009 | Langhals et al. |
| 2009/0247727 A1 | 10/2009 | Bernabe et al. |
| 2011/0319620 A1 | 12/2011 | Ishihara et al. |
| 2019/0040201 A1 | 2/2019 | Patil et al. |
| 2019/0092726 A1 | 3/2019 | Schulte, II et al. |
| 2019/0119240 A1 | 4/2019 | Royer et al. |
| 2019/0135750 A1 | 5/2019 | Croll et al. |
| 2021/0230133 A1 | 7/2021 | Werling et al. |

(Continued)

FOREIGN PATENT DOCUMENTS

| | | |
|---|---|---|
| CN | 102631794 A | 8/2012 |
| DE | 3213166 A1 | 10/1983 |
| EP | 0477539 A1 | 4/1992 |

(Continued)

OTHER PUBLICATIONS

Basosca, I. et al., "Comparative study of polyimides containing different flexible linkages", J. Iran Chem. Soc., vol. 9, 2012; pp. 901-910.
Bruma, M. et al., "Polyetherimides for Gas Separation Membranes", Molecular Crystals and Liquid Crystals, vol. 418, pp. 11-19, 2010.
Hu, Yu Lin et al., "An inexpensive and efficient synthetic method for the preparation of pyromellitic dianhydride promoted by ionic liquid", ARKIVOC, vol. 9, 2010; pp. 63-74.
International Search Report for International Application No. PCT/US2017/028263; International Filing Date Apr. 19, 2017; dated Aug. 24, 2017; 6 pages.

(Continued)

*Primary Examiner* — Kristin A Vajda
(74) *Attorney, Agent, or Firm* — CANTOR COLBURN LLP

(57) ABSTRACT

A method for producing an aromatic dianhydride includes reacting an aromatic diimide with a substituted or unsubstituted phthalic anhydride in an aqueous medium in the presence of an amine exchange catalyst to provide an aqueous reaction mixture including an N-substituted phthalimide, an aromatic tetraacid salt, and at least one of an aromatic triacid salt and an aromatic imide diacid salt. The method further includes removing the phthalimide from the aqueous reaction mixture by extracting the aqueous reaction mixture with an organic solvent using a single packed extraction column. The aromatic tetraacid salt is converted to the corresponding aromatic dianhydride. Aromatic dianhydrides prepared according to the method are also described.

17 Claims, No Drawings

(56) References Cited

U.S. PATENT DOCUMENTS

2021/0246124 A1     8/2021   Royer et al.

FOREIGN PATENT DOCUMENTS

| WO | 2017172593 A1 | 5/2017 |
| WO | 2017189293 A1 | 11/2017 |

OTHER PUBLICATIONS

International Search Report for the corresponding International Application No. PCT/US2019/030810; International Filing Dtae: May 6, 2019; dated Jul. 30, 2019. 5 pages.

Pinzow, Leonard, "Characteristics of a pulsed packed, liquid-liquid extraction column", Calhoun: The NPS Institutional Archive, Retrieved from the Internet on Sep. 20, 2018; http://hdl.handle.net/10945/13989; Jan. 1, 1957; pp. 1-105.

Rauber, Johannes, "Design Practice For Packed Liquid Liquid Extraction Columns", Sulzer, Retrieved from the Internet on Sep. 20, 2018; http://folk.ntnu.no/skoge/prost/proceedings/aiche-2006/data/papers/P73337.pdf; Jan. 1, 2006; pp. 1-12.

Schwartz, W.T. "A Novel Route to Aryl Diether Dianhydrides", High Performance Polymers, vol. 2, No. 3, 1990; pp. 189-196.

Wei, Haibing et al., "Comparative Study on Polyimides from Isomeric 3,3'-, 3,4'-, and 4,4'- Linked Bis(thioether anhydride)s", Journal of Polymer Science Part A: Polymer Chemistry, vol. 49, 2011; pp. 2484-2494.

Written Opinion for the corresponding International Application No. PCT/US2019/030810; International Filing Date: May 6, 2019; dated Jul. 30, 2019. 9 pages.

Written Opinion of the International Searching Authority for International Application No. PCT/US2017/028263; International Filing Date Apr. 19, 2017; dated Aug. 24, 2017; 9 pages.

Yoon, Chong-Bok et al., "Facile synthesis of new NLO-functionalized polyimides via Mitsunobu reaction", Journal Material Chemistry, vol. 9; 1999; pp. 2339-2344.

International Search Report for the corresponding International Application No. PCT/US2019/035325; International Filing Date: Jun. 4, 2019; dated Jul. 24, 2019. 6 pages.

Written Opinion for the corresponding International Application No. PCT/US2019/035325; International Filing Date: Jun. 4, 2019; dated Jul. 24, 2019. 6 pages.

International Search Report for International Application No. PCT/US2019/031972; International Filing Date May 13, 2019; dated Jul. 8, 2019; 8 pages.

Written Opinion for International Application No. PCT/US2019/031972; International Filing Date May 13, 2019; dated Jul. 8, 2019; 12 pages.

International Search Report for International Application No. PCT/US2019/037182; International Filing Date Jun. 14, 2019; dated Aug. 26, 2019; 6 pages.

Written Opinion for International Application No. PCT/US2019/037182; International Filing Date Jun. 14, 2019; dated Aug. 26, 2019; 9 pages.

METHOD FOR ISOLATION OF AN AROMATIC DIANHYDRIDE AND AROMATIC DIANHYDRIDES PREPARED BY THE METHOD

CROSS-REFERENCE TO RELATED APPLICATIONS

This application is a National Stage application of PCT/US2019/037182, filed Jun. 14, 2019, which claims benefit of European Application No. 18178321.8 filed on Jun. 18, 2018, both of which are incorporated by reference herein in their entirety.

BACKGROUND

Polyetherimides are a class of high performance polymers that can be processed to make molded articles, fibers, films, foams, and the like. Polyetherimides further have high strength, toughness, heat resistance, modulus, and broad chemical resistance, and so are widely used in industries as diverse as automotive, telecommunication, aerospace, electrical/electronics, transportation, and healthcare. Polyetherimides have shown versatility in various manufacturing processes, proving amenable to techniques including injection molding, extrusion, and thermoforming, to prepare various articles.

A number of processes for making polyetherimides have been disclosed. Two processes which have been of particular interest are the so-called melt polymerization and solution polymerization processes. Solution polymerization is generally conducted by reacting an aromatic dianhydride and an organic diamine in an inert solvent at elevated temperatures to form an amide-acid polymer via ring opening of the anhydride by nucleophilic attack of the diamine. The polyamide-acid is then formed into a polyetherimide by removal of water, for example by azeotropic distillation.

Aromatic dianhydrides are thus important to the production of polyetherimides. The aromatic dianhydrides can be prepared using an exchange reaction between an aromatic bisimide and a substituted or unsubstituted phthalic anhydride. In addition to dianhydride, the exchange reaction often produces various by-products which result in decreased yields of the dianhydride.

Accordingly, there remains a need for an improved method for producing and isolating dianhydrides that can provide high yields and minimize by-product formation.

BRIEF DESCRIPTION

A method for producing an aromatic dianhydride comprises reacting an aromatic diimide with a substituted or unsubstituted phthalic anhydride in an aqueous medium in the presence of an amine exchange catalyst under conditions effective to provide an aqueous reaction mixture comprising an N-substituted phthalimide, an aromatic tetraacid salt, and at least one of an aromatic triacid salt and an aromatic imide diacid salt, wherein the reacting is at a reaction temperature that is 140 to 250° C. and a reaction pressure of 1.13 to 2.16 MPa (150 to 300 psig), preferably 1.48 to 1.82 MPa (200 to 250 psig); removing the phthalimide from the aqueous reaction mixture by extracting the aqueous reaction mixture with an organic solvent in a single packed extraction column comprising a structured metal v-shaped packing; and converting the aromatic tetraacid salt to the corresponding aromatic dianhydride.

An aromatic dianhydride made by the method of any of claims 1 to 17, wherein the aromatic dianhydride has an imide anhydride content of 0.1 to 3 wt %, or 0.5 to 3 wt %, or 0.5 to 2.5 wt %, or 0.5 to 2 wt %, or 0.6 to 1.6 wt %, or 0.7 to 1.3 wt %, or 0.8 to 1.2 wt % imide anhydride, based on the total weight of the aromatic dianhydride.

The above described and other features are exemplified by the following detailed description.

DETAILED DESCRIPTION

The present inventors have discovered that use of a modified extraction procedure for isolation of an aromatic dianhydride can increase the overall dianhydride conversion and yield. In particular, the extraction procedure for isolation of an aromatic dianhydride of the present disclosure includes a single packed extraction column including a structured metal v-shaped packing material. The isolated aromatic dianhydrides advantageously have reduced amounts of imide anhydride by-products. The isolated aromatic dianhydrides produced by this method are also advantageously consistent, or uniform, in term of their composition, meaning that the imide anhydride content consistently falls within a certain range.

Accordingly, a method for producing an aromatic dianhydride represents an aspect of the present disclosure. The method comprises reacting an aromatic diimide (also referred to as an "aromatic bisimide" or "bisimide") with a substituted or unsubstituted phthalic anhydride in an aqueous medium in the presence of an amine exchange catalyst and under conditions effective to provide an aqueous reaction mixture.

The aromatic bisimide can be of the formula (1)

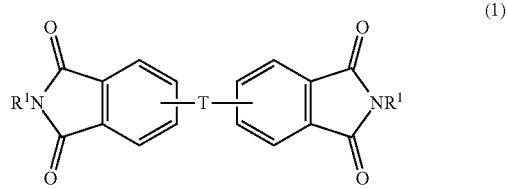

wherein T is $-O-$, $-S-$, $-C(O)-$, $-SO_2-$, $-SO-$, $-C_yH_{2y}-$ wherein y is an integer from 1 to 5 or a halogenated derivative thereof or $-O-Z-O-$, wherein Z is an aromatic $C_{6-24}$ monocyclic or polycyclic moiety optionally substituted with 1 to 6 $C_{1-8}$ alkyl groups, 1 to 8 halogen atoms, or a combination comprising at least one of the foregoing. In an aspect, the $R^1$ is a monovalent $C_{1-13}$ organic group.

In an aspect, T is $-O-$ or a group of the formula $-O-Z-O-$ wherein the divalent bonds of the $-O-$ or the $-O-Z-O-$ group are in the 3,3', 3,4', 4,3', or the 4,4' positions. Exemplary groups Z include groups of formula (2)

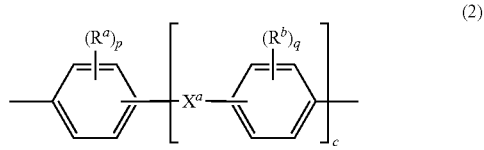

wherein $R^a$ and $R^b$ are each independently the same or different, and are a halogen atom or a monovalent $C_{1-6}$ alkyl group, for example; p and q are each independently integers of 0 to 4; c is 0 to 4; and $X^a$ is a bridging group connecting the hydroxy-substituted aromatic groups, where the bridging group and the hydroxy substituent of each $C_6$ arylene group are disposed ortho, meta, or para (specifically para) to each other on the $C_6$ arylene group. The bridging group $X^a$ can be a single bond, —O—, —S—, —S(O)—, —S(O)₂—, —C(O)—, or a $C_{1-18}$ organic bridging group. The $C_{1-18}$ organic bridging group can be cyclic or acyclic, aromatic or non-aromatic, and can further comprise heteroatoms such as halogens, oxygen, nitrogen, sulfur, silicon, or phosphorous. The $C_{1-18}$ organic group can be disposed such that the $C_6$ arylene groups connected thereto are each connected to a common alkylidene carbon or to different carbons of the $C_{1-18}$ organic bridging group. A specific example of a Group Z is a divalent Group of the formula (3a) or (3b)

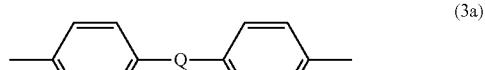

(3a)

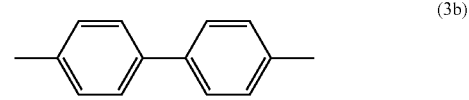

(3b)

wherein Q is —O—, —S—, —C(O)—, —SO₂—, —SO—, —P(R$^a$)(=O)— wherein R$^a$ is a $C_{1-8}$ alkyl or $C_{6-12}$ aryl, or —$C_yH_{2y}$— wherein y is an integer from 1 to 5 or a halogenated derivative thereof (including a perfluoroalkylene group). Exemplary dihydroxy aromatic compounds from which Z can be derived include but are not limited to 2,2-bis(2-hydroxyphenyl)propane, 2,4'-dihydroxydiphenylmethane, bis(2-hydroxyphenyl)methane, 2,2-bis-(4-hydroxyphenyl)propane ("bisphenol A" or "BPA"), 1,1-bis-(4-hydroxyphenyl)ethane, 1,1-bis-(4-hydroxyphenyl)propane, 2,2-bis-(4-hydroxyphenyl)pentane, 3,3-bis-(4-hydroxyphenyl)pentane, 4,4'-dihydroxybiphenyl, 4,4'-dihydroxy-3,3,5, 5'-tetramethylbiphenyl, 2,4'-dihydroxybenzophenone, 4,4'-dihydroxydiphenylsulfone, 2,4'-dihydroxydiphenylsulfone, 4,4'-dihydroxydiphenylsulfoxide, 4,4'-dihydroxydiphenylsulfide, hydroquinone, resorcinol, 3,4-dihydroxydiphenylmethane, 4,4'-dihydroxybenzophenone, 4,4'-dihydroxydiphenylether, and the like, or a combination comprising at least one of the foregoing. In an aspect, Z is derived from bisphenol A, such that Q in the above formula is, 2,2-isopropylidene. Thus in an aspect, Z is 2,2-(4-phenylene) isopropylidene. In an aspect, R¹ is a $C_{1-4}$ alkyl group, for example a methyl group, an ethyl group, a propyl group, or a butyl group, preferably a methyl group.

In an aspect, the aromatic bisimide comprises 4,4'-bisphenol A-bis-N-methylphthalimide, 3,4'-bisphenol A-bis-N-methylphthalimide, 3,3'-bisphenol A-bis-N-methylphthalimide, or a combination comprising at least one of the foregoing.

The substituted or unsubstituted phthalic anhydride can be of the formula (4)

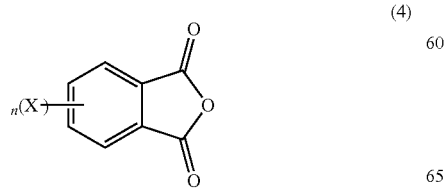

(4)

wherein X is fluoro, chloro, bromo, iodo, nitro, or a combination comprising at least one of the foregoing, and n is 0 or 1. In an aspect, n is 0 and the phthalic anhydride is an unsubstituted phthalic anhydride. In an aspect, n is 1, and the phthalic anhydride is a substituted phthalic anhydride, wherein X is fluoro, chloro, bromo, iodo, nitro, or a combination comprising at least one of the foregoing. In an aspect, the substituted or unsubstituted phthalic anhydride comprises phthalic anhydride, 3-halophthalic anhydride, 4-halophthalic anhydride, 3-nitrophthalic anhydride, 4-nitrophthalic anhydride, or a combination comprising at least one of the foregoing. Specific examples of suitable halophthalic anhydrides include 3-fluorophthalic anhydride, 4-fluorophthalic anhydride, 3-chlorophthalic anhydride, 4-chlorophthalic anhydride, 3-bromophthalic anhydride, 4-bromophthalic anhydride, 3-iodophthalic anhydride, and 4-iodophthalic anhydride. In an aspect, the substituted or unsubstituted phthalic anhydride is preferably phthalic anhydride.

Reacting the aromatic bisimide with the substituted or unsubstituted phthalic anhydride is carried out in aqueous medium in the presence of an amine exchange catalyst. The amine exchange catalyst can include a ($C_{1-20}$ alkyl)-substituted amine, preferably a tri($C_{1-20}$ alkyl)amine. In an aspect, the amine exchange catalyst is preferably triethylamine. In an aspect, the initial molar ratio of amine exchange catalyst to the phthalic anhydride is 1:1 to 2:1.

The reacting is further carried out under conditions effective to provide an aqueous reaction mixture. Effective conditions can include reacting at a reaction temperature that is 140 to 250° C., for example 160 to 200° C., and a reaction pressure of 150 to 300 psig (1.13 to 2.16 megapascals (MPa)), preferably 200 to 250 psig (1.47 to 1.82 MPa), more preferably 200 to 230 psig (1.47 to 1.68 MPa).

In an aspect, the initial molar ratio of phthalic anhydride to aromatic bisimide is 4:1 to 20:1, or 4:1 to 10:1, or 4:1 to 8:1, or 4:1 to 5.5:1, or 4:1 to 5.5:1. Without wishing to be bound by theory, it is believed that a molar ratio of phthalic anhydride to aromatic bisimide of 4:1 to 5:1 can be preferred at least for economic reasons.

The aqueous reaction mixture provided by reacting the aromatic bisimide with the substituted or unsubstituted phthalic anhydride comprises an N-substituted phthalimide, an aromatic tetraacid salt, and at least one of an aromatic triacid salt and an aromatic imide diacid salt.

The N-substituted phthalimide can be of the formula

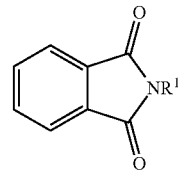

wherein R¹ is as defined above. The N-substituted phthalimide can be an N—($C_{1-13}$ alkyl) substituted phthalimide, preferably an N—($C_{1-6}$ alkyl) substituted phthalimide, for example N-methyl phthalimide.

In an aspect, the aromatic tetra acid salt is of the formula (5)

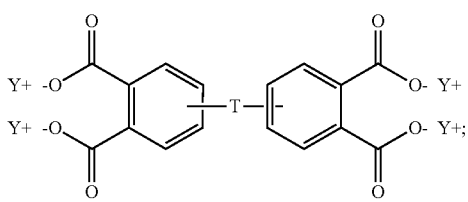

the aromatic triacid salt is of the formula (6)

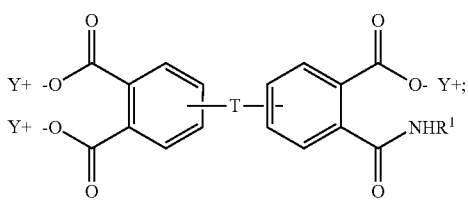

and the aromatic imide-diacid salt is of the formula (7)

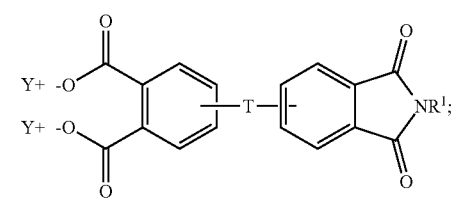

wherein T can be as described above, and is preferably —O—, —S—, —C(O)—, —SO$_2$—, —SO—, —C$_y$H$_{2y}$— wherein y is an integer from 1 to 5 or a halogenated derivative thereof or —O—Z—O—, wherein Z is an aromatic C$_{6-24}$ monocyclic or polycyclic moiety optionally substituted with 1 to 6 C$_{1-8}$ alkyl groups, 1 to 8 halogen atoms, or a combination comprising at least one of the foregoing, R$^1$ is a C$_{1-13}$ organic group, or a C$_{1-4}$ alkyl group, preferably a methyl group, and Y is a cationic group, preferably a C$_{1-20}$ trialkylammonium group (i.e., an aromatic tetraacid ammonium salt, triacid ammonium salt, and imide diacid ammonium salt), or a proton (i.e., the aromatic tetraacid ammonium salt, triacid ammonium salt, and imide diacid ammonium salt can be in the form of the corresponding aromatic tetraacid, triacid, and imide acid, respectively). In an aspect, Y is a C$_{1-20}$ trialkylammonium group, preferably a triethylammonium group. Thus, in an aspect, the aromatic tetra acid salt can be an aromatic tetra acid triethylamine salt, the aromatic triacid salt can be an aromatic triacid triethylamine salt, and the aromatic imide-diacid salt can be an aromatic imide-diacid triethylamine salt. In an aspect, T is —O—Z—O—, wherein Z is derived from bisphenol A. The divalent bonds of the —O—Z—O— group are in the 3,3', 3,4', 4,3', or the 4,4' positions. For simplicity, the aromatic triacid salt of the formula (6) and the aromatic imide-diacid salt of the formula (7) can collectively be referred to as "imide anhydride species", as it will be understood by one of skill in the art that these species are precursors to the imide anhydride of formula (9), described below.

In an aspect, the aqueous reaction mixture can further comprise at least one of the aromatic bisimide and the substituted or unsubstituted phthalic anhydride. In an aspect, the aqueous reaction mixture can further comprise the substituted or unsubstituted phthalic anhydride, preferably wherein the substituted or unsubstituted phthalic anhydride is in the form of the corresponding ring-opened diacid salt, for example a corresponding ring-opened diacid C$_{1-20}$ trialkylammonium salt.

The method further comprises removing the N-substituted phthalimide and any residual aromatic bisimide from the aqueous reaction mixture by extracting the aqueous reaction mixture with an organic solvent. In an aspect, the organic solvent is a (C$_{1-6}$ alkyl)benzene, benzene, or a halogenated aromatic solvent. For example, the organic solvent can comprise toluene, xylene, chlorobenzene, ortho-dichlorobenzene, or a combination comprising at least one of the foregoing. In an aspect, the organic solvent can optionally comprise 0 to 15 weight percent, or 1 to 10 weight percent, or 2 to 8 weight percent of a tri(C$_{1-6}$ alkyl)amine, preferably triethylamine. In an aspect, the volumetric ratio of the organic solvent to the aqueous medium is 0.3:1 to 3:1, or 0.5:1 to 1:1, or 0.75:1 to 1:1.

The extracting to remove the phthalimide is in a single packed extraction column. When using an extraction column, the aqueous phase from the exchange reaction is typically fed continuously into the top of the extraction column while the organic solution is fed continuously into the bottom of the exchange column. It is noted that whether the aqueous phase is fed to the top or bottom of the extraction column will depend on the relative densities of the aqueous phase and the organic solvent, as can be determined by one of skill in the art. For example, when an organic solvent having a density less than the density of the aqueous phase is used, the configuration will be as described above. Alternatively, when an organic solvent having a density greater than the density of the aqueous phase is used, the aqueous phase will be fed continuously to the bottom of the column, and the organic phase will be fed continuously to the top of the column.

The single packed extraction column of the present disclosure includes a structured packing material, in particular a structured metal packing material. "Structured packing" means packing wherein individual members have a specific orientation relative to each other and to the column axis. The structured metal packing material can be a structured metal v-shaped packing (SMVP). The packing material can have a certain specific area, for example, 27-95 square feet per cubic foot, preferably 34-68 square feet per cubic foot.

The extracting is a continuous process, wherein the aqueous phase and the organic solvent are continuously fed to the extraction column. The extracting is carried out at an extraction temperature of 100 to 250° C., for example 100 to 200° C., for example 110 to 180° C., or 115 to 175° C. The extracting can be for a period of time of, for example, 30 seconds to 3 hours, or 5 minutes to 3 hours, or 20 minutes to 3 hours, or 20 minutes to 2 hours, or 20 minutes to 1 hour, or 1 to 3 hours, or 1 to 2 hours, or 1 to 1.5 hours, preferably 5 minutes to 3 hours, or 20 minutes to 2 hours, or 20 minutes to 1 hour. In an aspect, conversion of the aromatic bisimide to aromatic dianhydride (i.e., as the tetraacid salt) can be greater than 70%, or greater than 75%, or greater than 78% or greater than 80% at the extracting. In an aspect, conversion of the aromatic bisimide to aromatic dianhydride can be 70 to 90%, or 75 to 90%, or 78 to 90%, or 80 to 90% after extracting with the organic solvent. In an aspect, the desired conversion is obtained at a desired bisimide:phthalic anhydride molar ratio and percent solids (also referred to as "solids content"). As used herein, the term "solids content" is defined as the weight of the aromatic bisimide, the aromatic dianhydride, and, when present, the aromatic imide-anhydride, the aromatic tetra acid salt, the aromatic triacid salt, the aromatic imide-diacid salt, and the corresponding ring-closed derivatives thereof, relative to the total weight of the reaction mixture. In an aspect, the aqueous reaction mixture can have a solids content of 5 to 26 weight percent, or 10 to 20 weight percent, or 13 to 23 weight percent, or 13 to 17 weight percent, or 13 to 16 weight percent. Within this range, the solids content can be at least 5, 10, 12, 15, 17, or 18 weight percent. Also within this range, the solids content can be less than or equal to 24, 23, 19, or 16 weight percent.

The present inventors have further advantageously discovered that various process parameters can be adjusted in order to achieve the desired conversion to the aromatic dianhydride. For example, the method can use a volumetric ratio of the organic solvent to the aqueous reaction mixture of 0.5:1 to 1.5:1, preferably 0.8:1 to 1:1. For example, the single packed extraction column can have a capacity of 200 to 600 gallons per hour per square foot, preferably 430 to 560 Gph/sq ft. "Capacity" refers to the total flow into the column (e.g., flow of the combined aqueous and organic streams) per unit area. For example, the dispersed phase volumetric holdup (also referred to as the dispersed phase volumetric fraction) can be at least 3%, preferably 5%, more preferably 5 to 10%, even more preferably 6 to 8%. As used herein, the term "dispersed phase holdup" refers to a measure of the volume of the dispersed phase in the column compared to the total volume of the liquid in the column. Accordingly, for example, a dispersed phase holdup of at least 5% means that at least 5% of the total volume of liquid in the column is the dispersed phase. The dispersed phase comprises the organic solution, thus the column comprises droplets of the organic solution dispersed in a continuous phase comprising the aqueous phase. For example, the continuous phase can have a residence time, when maintaining the capacity and organic to aqueous ratios set forth herein, of less than one hour, preferably less than 45 minutes. The method of the present disclosure can include at least one of the aforementioned process parameters, and can comprise two, three of four of the process parameters. Each of the recited process parameters can be used in any combination thereof. Furthermore, other process parameters in addition to those listed above can be used in the method of the present disclosure.

In an aspect, the method comprises at least each of the following process parameters: a volumetric ratio of the organic solvent to the aqueous reaction mixture of 0.5:1 to 1.5:1, preferably 0.8:1 to 1:1; an extraction column operating capacity of 200 to 600 Gph/Sq·ft, preferably 430 to 560 Gph/sq ft; a dispersed phase hold up of greater than 5%, preferably 6 to 8%; and a continuous phase residence time of less than one hour, preferably less than 45 minutes.

In an aspect, the method can further comprise an additional process parameter wherein an organic solvent flow rate of at least 35 kilograms per hour is used when operating the extraction column, and when the extraction column has a diameter of 4 inches or less.

In an aspect, the extracting provides an extracted aqueous stream comprising the aromatic tetraacid salt and optionally the aromatic triacid salt, the aromatic imide-diacid salt, a substituted or unsubstituted phthalic acid salt, or a combination comprising at least one of the foregoing, and an organic stream comprising the organic solvent, N-substituted phthalimide, and optionally unreacted aromatic bisimide.

In an aspect, the method can further include repeating the extracting of the aqueous phase with an organic phase to further convert imide anhydride to aromatic dianhydride (which can be in the form of the tetra-acid salt) in order to provide the desired conversion, for example greater than 70%, or greater than 75%, or greater than 78%, or greater than 80%. Repeating the extracting can include any number of additional extractions.

The method further comprises converting the aromatic tetraacid salt to the corresponding aromatic dianhydride. Converting the aromatic tetraacid salt to the corresponding aromatic dianhydride occurs in separate equipment positioned downstream of the extraction column. The amount of time as well as the temperature for the converting is generally dependent upon the identity of the dianhydride and can be readily determined by one of ordinary skill in the art. For example, useful temperatures can be 160 to 300° C., or 180 to 240° C. or 200 to 220° C. The conversion of the aromatic tetraacid salt to dianhydride is a cyclization with the concurrent formation of water and evolution of a free amine species derived from the cationic group Y. Alternatively, the tetraacid salt can be condensed by refluxing in the presence of a dehydrating agent, for example acetic anhydride. In an aspect, a temperature of 100 to 225° C. and a pressure of 0 MPa to 1 MPa, for example 0 to 0.5 MPa, or 0 to 0.2 MPa, can be used. It is also noted that any phthalic anhydride present in the form of the corresponding ring-opened diacid salt present can be converted to phthalic anhydride by cyclization with the concurrent formation of water and evolution of a free amine species derived from the cationic group under the same conditions described above for the conversion of the aromatic tetraacid salt. Advantageously, trace water, catalyst, and other residual volatile materials such as phthalic anhydride can also be removed as vapor under the conditions utilized for conversion. In an aspect, the converting can provide a product mixture comprising the aromatic dianhydride, and an aromatic imide-anhydride, for example formed from the cyclization of the above-described imide anhydride species (e.g., according to formulas (6) and (7)).

The aromatic dianhydride can be of the formula (8)

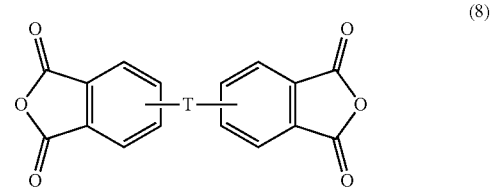

wherein T can be as defined above. In an aspect, T is —O—Z—O—, preferably wherein Z is derived from bisphenol A (i.e., Z is 2,2-(4-phenylene)isopropylidene). Illustrative examples of aromatic dianhydrides include 3,3-bis[4-(3,4-dicarboxyphenoxy)phenyl]propane dianhydride; 4,4'-bis(3,4-dicarboxyphenoxy)diphenyl ether dianhydride; 4,4'-bis(3,4-dicarboxyphenoxy)diphenyl sulfide dianhydride; 4,4'-bis(3,4-dicarboxyphenoxy)benzophenone dianhydride; 4,4'-bis(3,4-dicarboxyphenoxy)diphenyl sulfone dianhydride; 2,2-bis[4-(2,3-dicarboxyphenoxy)phenyl]propane dianhydride; 4,4'-bis(2,3-dicarboxyphenoxy)diphenyl ether dianhydride; 4,4'-bis(2,3-dicarboxyphenoxy)diphenyl sulfide dianhydride; 4,4'-bis(2,3-dicarboxyphenoxy)benzophenone dianhydride; 4,4'-bis(2,3-dicarboxyphenoxy)diphenyl sulfone dianhydride; 4-(2,3-dicarboxyphenoxy)-4'-(3,4-dicarboxyphenoxy)diphenyl-2,2-propane dianhydride; 4-(2,3-dicarboxyphenoxy)-4'-(3,4-dicarboxyphenoxy)diphenyl ether dianhydride; 4-(2,3-dicarboxyphenoxy)-4'-(3,4-dicarboxyphenoxy)diphenyl sulfide dianhydride; 4-(2,3-dicarboxyphenoxy)-4'-(3,4-dicarboxyphenoxy)benzophenone dianhydride; and, 4-(2,3-dicarboxyphenoxy)-4'-(3,4-dicarboxyphenoxy)diphenyl sulfone dianhydride.

The aromatic imide-anhydride can be of the formula (9)

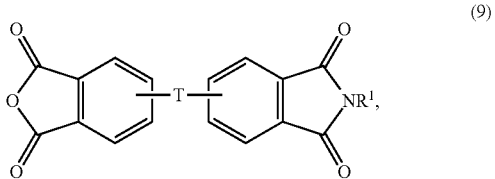

(9)

wherein T and $R^1$ are as defined above. In an aspect, T is —O—Z—O—, wherein Z is derived from bisphenol A. In an aspect, $R^1$ is preferably a methyl group.

In an aspect, the method comprises reacting an aromatic bisimide with a substituted or unsubstituted phthalic anhydride in an aqueous medium in the presence of an amine exchange catalyst at a reaction temperature that is 160 to 270° C., or 160 to 250° C., 160 to 200° C. to form an aqueous reaction mixture; and removing the phthalimide from the aqueous reaction mixture by extracting with an organic solvent in a single packed extraction column.

An aromatic dianhydride prepared according to the above-described method is another aspect of the present disclosure. The aromatic dianhydride can be of formula (8) above. In an aspect, the aromatic dianhydride can have an imide-anhydride content of less than or equal to 4 wt %, based on the total weight of the aromatic dianhydride, wherein the imide-anhydride can be according to formula (9) above. In a particularly advantageous feature, the imide anhydride content of the aromatic dianhydride produced by the method described herein can be uniform or consistent. For example, the imide anhydride content can be within a certain range, for example 0.1 to 3 wt %, or 0.5 to 3 wt %, or 0.5 to 2.5 wt %, or 0.5 to 2 wt %, or 0.6 to 1.6 wt %, or 0.7 to 1.3 wt %, or 0.8 to 1.2 wt %. The desired uniform imide anhydride content can be obtained at a particular phthalic anhydride:bisimide molar ratio, for example of 4:1 to 5:1. Without wishing to be bound by theory, manipulation of the phthalic anhydride:bisimide molar ratio (e.g., to 6:1 or 7:1) will result in increased conversion to aromatic dianhydride and lower imide anhydride content. This is a particularly advantageous feature of the present disclosure because imide anhydride is a monofunctional reactant from the standpoint of a polymerization to form poly(etherimide). Thus, any imide anhydride present will act as a chain stopper during a polymerization reaction, making it difficult to achieve high molecular weight poly(etherimide) from the aromatic dianhydride. High molecular weight poly(etherimide) can provide many advantages, thus providing a higher purity aromatic dianhydride which in particular includes very low amounts of imide anhydride chain stopper is especially advantageous.

An improved method for isolation of an aromatic dianhydride is provided herein wherein a single packed extraction column is employed containing a structured metal v-shaped packing material. The method also advantageously employs extracting at carefully selected extraction conditions in order to increase overall conversion to dianhydride and increase the yield of the isolated aromatic dianhydride. Therefore, a substantial improvement in methods of isolating an aromatic dianhydride is provided by the present disclosure.

This disclosure is further illustrated by the following examples, which are non-limiting.

EXAMPLES

In the present Examples, the bisimide/dianhydride exchange reaction was carried out using the following general procedure.

In a typical procedure, a reactor was charged with 4,4'-bisphenol A-bis-N-methylphthalimide (which can also include small amounts of 3,4'-bisphenol A-bis-N-methylphthalimide and 3,3'-bisphenol A-bis-N-methylphthalimide) and phthalic anhydride in a molar ratio of phthalic anhydride to bisimide of 4.2:1. The reaction was conducted in the presence of a triethylamine (TEA) exchange catalyst. The TEA was used in a TEA:phthalic anhydride molar ratio of 1.25:1. Water was used as the solvent to provide an aqueous reaction mixture having a solids content (% solids) in the range of 14 to 15%. The bisimide/dianhydride exchange reaction was carried out at a temperature of 160 to 165° C. for 1 hour and at a pressure of 160 psig. For simplicity of the discussion that follows, "N-methylphthalimide" will be referred to as "PI", the "4,4'-bisphenol A-bis-N-methylphthalimide" mixture will be referred to as "BI", and the "4,4'-bisphenol A dianhydride" product will be referred to as "DA".

The following examples were conducted using a 4 inch diameter extraction column. The aqueous reaction mixture outlet from the reactor was preheated and continuously fed into the top of the extraction column. The aqueous reaction mixture entering the extraction column had the following composition: 6.06 wt % PI; 11.284 wt % phthalic anhydride; 7.67 wt % DA; 5.32 wt % imide anhydride (IA); 1.41 wt % residual BI; 53.4 wt % water; and 14.86 wt % TEA exchange catalyst. This composition corresponds to the following molar fractions: 0.541 DA; 0.365 IA; and 0.094 BI, based on BI molar equivalents.

Toluene containing 5 weight percent (wt %) TEA was used as the organic solvent and was also preheated and continuously fed into the bottom of the extraction column. The process parameters that were examined include extractor capacity, organic solvent:aqueous medium ratio, toluene flow rate, and dispersed phase holdup. Dispersed phase holdup was measured using the shutoff valve method. The column packing material was structured sheet metal V-shaped packing (SMVP) material.

Table 1 shows a summary of experiments that were conducted at lower capacity (e.g., capacity of 220-230 gallons per hour per square foot (Gph/sq ft)). The results shown in Table 1 indicate that the imide anhydride lost to back reaction can be 16-34% depending on the operational parameters employed. For example, higher toluene flow rates (e.g., greater than 35 kg/hr) resulted in only 16% imide anhydride lost to back reaction.

Experiments were also conducted to study the effect of toluene flow rate at higher capacity (440-550 Gph/sq ft). These results are also shown in Table 1. These results show that imide anhydride lost to back reaction can be varied from 16-23% based on the toluene flow rate employed. For example, a toluene flow rate of greater than about 65 kg/hr at high capacity can lead to significant improvement in the amount of imide anhydride lost to back reaction (i.e., reduction to about 14-16%).

In Table 1, "Capacity" refers to the total flow into the column (e.g., flow of the combined aqueous and organic streams) per unit area. "Aqueous flow rate" refers to the rate at which the aqueous phase enters the column from the reactor. "Organic flow rate" refers to the rate at which the organic phase enters the column. "IA lost to organic" refers to the amount of imide-anhydride species that is solubilized in the organic phase, and thus extracted from the column with phthalamide (PI) and bisimide (BI). "IA lost to back reaction" refers to the amount of the imide-anhydride species that are converted back to BI starting material, and then extracted into the organic phase and removed from the column. "IA to DA" refers to the conversion of the imide-anhydride species to the desired dianhydride tetra-acid salt. "IA remaining in aq" refers to the amount of imide-anhydride species in the aqueous phase during the extraction (where imide anhydride species is defined above, and can include imide anhydride, as well as the corresponding diacid imide, triacid amide, and salts thereof). "BI extraction efficiency" and "PI extraction efficiency" refer to the amount of BI and PI, respectively that are removed from the column during the extraction based on the weight of each in the feed. It is noted that some small amount of BI or PI or both can remain in the aqueous phase.

Extraction was carried out at a temperature of 170 to 180° C. and at a pressure of 200 to 250 psig.

TABLE 1

| Ex. | Capacity (Gph/sq ft) | Aq. Flowrate (kg/hr) | Org. Flow rate (kg/hr) | Org./Aq. Vol. Ratio | Residence time of Aq. Phase (min) | Column Temp (° C.) | IA lost to organic phase (mol %) |
|---|---|---|---|---|---|---|---|
| 1 | 230 | 39.2 | 35.1 | 1 | 114 | 171-174 | 1 |
| 2 | 220 | 35.4 | 37.5 | 1.4 | 105 | 171-174 | 2 |
| 3 | 230 | 44.4 | 34.3 | 0.8 | 115 | 171-174 | 0.3 |
| 4 | 460 | 79.4 | 64.3 | 1 | 55 | 170-180 | 1 |
| 5 | 460 | 73.9 | 60.6 | 1 | 56 | 171-174 | 1 |
| 6 | 550 | 84.4 | 78.8 | 1 | 44 | 171-174 | 0.2 |
| 7 | 440 | 67.2 | 77.5 | 1.4 | 46 | 171-174 | 1 |
| 8 | 460 | 84.9 | 61.5 | 0.8 | 60 | 171-174 | 0.3 |

| Ex. | IA lost to back reaction (mol %) | IA to DA (mol %) | Overall DA Molar Yield (mol %) | IA remaining in aq (mol %) | BI extraction efficiency (wt %) | PI extraction efficiency (wt %) | IA relative to DA (wt. %) |
|---|---|---|---|---|---|---|---|
| 1 | 23 | 74 | 81.1 | 3 | 96 | 98 | 1.23 |
| 2 | 16 | 80 | 83.3 | 2 | 95 | 98.8 | 0.95 |
| 3 | 34 | 63 | 77.1 | 3 | 97 | 98 | 1.22 |
| 4 | 23 | 74 | 81.1 | 3 | 96 | 98 | 1.4 |
| 5 | 21 | 75 | 81.5 | 3 | 96 | 98 | 1.22 |
| 6 | 14 | 82 | 84.0 | 3 | 94 | 98 | 1.42 |
| 7 | 16 | 80 | 83.3 | 3 | 93 | 98.8 | 1.22 |
| 8 | 21 | 74 | 81.1 | 4 | 96 | 99 | 2 |

As described above, the inlet feed composition (i.e., the composition of the aqueous feed leaving the reactor and entering the extraction column) corresponded to the following molar fractions: 0.541 DA; 0.365 IA; and 0.094 BI. After conducting the extraction, the overall yield of the desired DA was greater than 60% as shown in Table 1. For example, looking at example 7 above, the overall DA yield can be calculated as 0.541 moles of DA+(0.365 moles of IA*0.8 moles of IA converted to DA). Thus, the product stream of example 7 achieves 83.3% overall DA molar yield (0.541+(0.365*0.80)=0.833*100=83.5% DA at the end of the extraction).

Additional experiments were conducted to study the effect of toluene flow rate on the imide anhydride species back reaction at constant aqueous flow rate. The results, which are summarized in Table 2, show that the amount of imide anhydride species lost to back reaction varies from 14-22%, resulting in an overall DA yield of 82.6 to 85.5%, depending on the toluene flow rate, the dispersed phase holdup, and the continuous phase residence time. Each of the parameters in Table 2 are as defined above for Table 1. "Dispersed phase holdup" refers to the volumetric holdup in the column (i.e., the amount of the total volume of the liquid in the column that is the dispersed phase).

TABLE 2

| Ex. | Capacity (gph/sq. ft) | Aq. flow rate (kg/hr) | Org. flow rate (kg/hr) | IA lost to Org. (mol %) | IA lost to back reaction (mol %) | IA to DA (mol %) | Overall DA Yield (mole %) | IA remaining in aq. (mol %) | Dispersed phase hold up (vol %) | Continuous phase residence time (min) |
|---|---|---|---|---|---|---|---|---|---|---|
| 9 | 460 | 73.9 | 60.6 | 1 | 21 | 75 | 82.9 | 3 | 5.2 | 56 |
| 10 | 530 | 75.7 | 85.8 | 0.5 | 14 | 83 | 85.5 | 3 | 7.1 | 41 |
| 11 | 420 | 75.5 | 49.8 | 0.4 | 22 | 75 | 82.6 | 3 | 3.4 | 76 |

The results provided by the present examples show that a dispersed phase holdup of 6-8% and a continuous phase residence time of 40 minutes will result in about 14% of imide anhydride lost to the back reaction.

Advantageously, the DA produced by the method of the present disclosure was reliably consistent in composition, in particular with respect to imide anhydride content. The aqueous stream obtained from the extraction column (i.e., after conducting the extraction) was subjected to thermal treatment under vacuum which consistently produced the desired aromatic dianhydride having an imide anhydride content of 1±0.2 wt %.

As a Comparative Example, the process of the present disclosure using a SMVP packed column was compared to a method using an extraction with a single GOODLOE packed extraction column. Reaction was carried out at a PA:BI molar ratio of 4.5:1 to 5:1 at a triethylamine TEA:PA molar ratio of 2:1. Solids content (% solids) was maintained in the range of 13 to 15%. The reaction was conducted at 170° C. at a pressure of 230 psig with a residence time of 1 hour. The aqueous feed was fed to the top of GOODLOE packed extraction column, and toluene containing 5 weight percent (wt %) TEA was continuously fed to the bottom of extraction column. The aqueous feed composition entering the extraction column was 45 mol % dianhydride as triethylammonium salts, 40 mol % IA as triethylammonium salts, and 15 mol % BI, all based on BI mole equivalents used in the reaction. Extraction was carried out with a temperature range of 145 to 170° C. with the pressure range of 200 to 250 psig.

Results from three comparative examples are shown in Table 3 below. Table 3 shows the amount of IA lost to back reaction (33 to 45 mole percent) and the resulting molar conversion of BI to DA (67 to 72%). As discussed above, the use of the single SMVP packed column resulted in 14 mole percent back reaction with a molar conversion of 84 to 85% BI to DA. Without wishing to be bound by theory, it is believed that the differences between the inventive examples and comparative examples can, at least in part, be attributed to the extraction in the comparative examples being less efficient, causing more BI to be formed, which cannot be converted to DA. Thus, the increased conversion of IA to DA in the SMVP packed column is believed to be due to the increased extraction efficiency.

TABLE 3

| Comparative Example | Organic:Aqueous ratio (Vol) | Maximum capacity (gph/Sq. ft) | Minimum capacity (gph/sq. ft) | IA lost to back rxn (mol %) | BI to DA Conversion (mol %) | IA relative DA (wt %) |
|---|---|---|---|---|---|---|
| C1 | 1.4 | 361.26 | 177.24 | 33 | 72 | 2.5 |
| C2 | 1.2 | 358.02 | 155.1 | 38 | 70 | 2.5 to 3 |
| C3 | 1 | 325.44 | 141 | 45 | 67 | 2.5 to 3 |

Thus, the use of a SMVP packed extraction column can offer several advantages, including >80% DA yield achieved using single column configuration operated in a conventional manner. The SMVP packed column can also have a better flowrate turndown ratio and aqueous/organic interface control, which helps in flexibility of running the plants at minimal and higher throughputs.

This disclosure further encompasses the following aspects.

Aspect 1: A method for producing an aromatic dianhydride, the method comprising reacting an aromatic diimide with a substituted or unsubstituted phthalic anhydride in an aqueous medium in the presence of an amine exchange catalyst under conditions effective to provide an aqueous reaction mixture comprising an N-substituted phthalimide, an aromatic tetraacid salt, and at least one of an aromatic triacid salt and an aromatic imide diacid salt, wherein the reacting is at a reaction temperature that is 140 to 250° C. and a reaction pressure of 1.13 to 2.16 MPa (150 to 300 psig), preferably 1.48 to 1.82 MPa (200 to 250 psig); removing the phthalimide from the aqueous reaction mixture by extracting the aqueous reaction mixture with an organic solvent in a single packed extraction column comprising a structured metal v-shaped packing; and converting the aromatic tetraacid salt to the corresponding aromatic dianhydride; wherein the aromatic diimide is of the formula

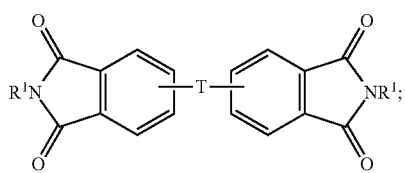

the substituted or unsubstituted phthalic anhydride is of the formula

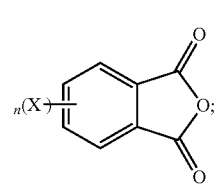

the N-substituted phthalimide is of the formula

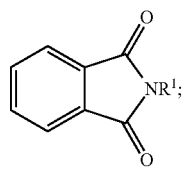

the aromatic tetraacid salt is of the formula

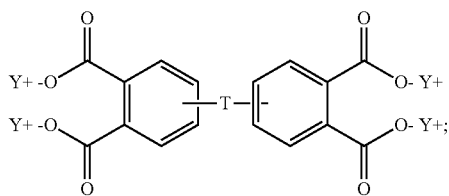

the aromatic triacid salt is of the formula

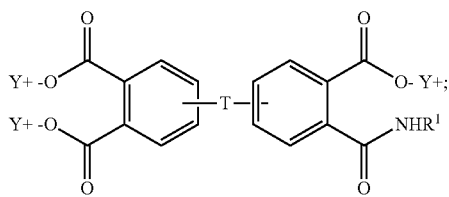

and the aromatic imide diacid salt is of the formula

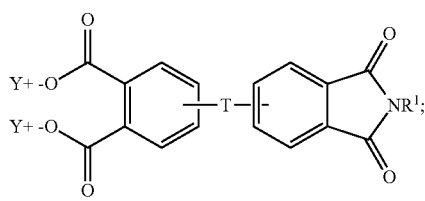

and the aromatic dianhydride is of the formula

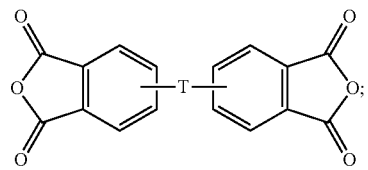

wherein in the forgoing formulas T is —O—, —S—, —C(O)—, —SO$_2$—, —SO—, —C$_y$H$_{2y}$— wherein y is an integer from 1 to 5 or a halogenated derivative thereof or —O—Z—O—, wherein Z is an aromatic $C_{6-24}$ monocyclic or polycyclic moiety optionally substituted with 1 to 6 $C_{1-8}$ alkyl groups, 1 to 8 halogen atoms, or a combination comprising at least one of the foregoing; $R^1$ is a monovalent $C_{1-13}$ organic group; X is fluoro, chloro, bromo, iodo, nitro, or a combination comprising at least one of the foregoing; n is 0 or 1; and Y is a cationic group, preferably a $C_{1-20}$ trialkylammonium group or a proton.

Aspect 2: The method of aspect 1, wherein conversion to the aromatic dianhydride is at least 75%, preferably at least 80%.

Aspect 3: The method of aspect 1 or 2, wherein the method comprises at least one of the following process parameters: (a) a volumetric ratio of the organic solvent to the aqueous reaction mixture of 0.5:1 to 1.5:1, preferably 0.8:1 to 1:1; (b) an extraction column operating capacity of 8.149 to 24.47 (m3/hr)/m2 (200 to 600 Gph/Sq·ft), preferably 17.520 to 22.817 (m3/hr)/m2 (430 to 560 Gph/sq ft); (c) a dispersed phase hold up of at least 3%, preferably 5%, more preferably 5 to 10%, even more preferably 6 to 8%; and (d) a continuous phase residence time of less than one hour, preferably less than 45 minutes.

Aspect 4: The method of aspect 3, wherein the method comprises process parameter (a).

Aspect 5: The method of aspect 3, wherein the method comprises process parameter (b).

Aspect 6: The method of aspect 3, wherein the method comprises process parameter (c).

Aspect 7: The method of aspect 3, wherein the method comprises process parameter (d).

Aspect 8: The method of aspect 3, wherein the method comprises at least two of the process parameters, or at least three of the process parameters, or at least four of the process parameters.

Aspect 9: The method of aspect 3, wherein the method comprises each of process parameters (a), (b), (c), and (d).

Aspect 10: The method of aspect 3, wherein the method comprises process parameters (a) and (b).

Aspect 11: The method of any of aspects 1 to 10, wherein the substituted or unsubstituted phthalic anhydride comprises phthalic anhydride, 3-halophthalic anhydride, 4-halophthalic anhydride, 3-nitrophthalic anhydride, 4-nitrophthalic anhydride, or a combination comprising at least one of the foregoing, preferably phthalic anhydride; and the exchange catalyst comprises a ($C_{1-20}$ alkyl)-substituted amine, preferably a tri($C_{1-20}$ alkyl)amine, more preferably triethylamine.

Aspect 12: The method of any of aspects 1 to 11, wherein the initial molar ratio of phthalic anhydride to aromatic diimide is 4:1 to 20:1, or 4:1 to 10:1, or 4:1 to 8:1, or 4:1 to 5.5:1.

Aspect 13: The method of any of aspects 1 to 12, wherein the initial molar ratio of amine exchange catalyst to the phthalic anhydride is 1:1 to 2:1.

Aspect 14: The method of any of aspects 1 to 13, wherein the aromatic diimide comprises 4,4'-bisphenol A-bis-N-methylphthalimide, 3,4'-bisphenol A-bis-N-methylphthalimide, 3,3'-bisphenol A-bis-N-methylphthalimide, or a combination comprising at least one of the foregoing; the aromatic dianhydride comprises 4,4'-bisphenol A-bis-dianhydride, 3,4'-bisphenol A-bis-dianhydride, 3,3'-bisphenol A-bis-dianhydride, or a combination comprising at least one of the foregoing; and the organic solvent comprises toluene, xylene, chlorobenzene, ortho-dichlorobenzene, or a combination comprising at least one of the foregoing, preferably toluene.

Aspect 15: The method of any of aspects 1 to 14, wherein the removing is at an extraction temperature of 100 to 250° C.

Aspect 16: The method of any of aspects 1 to 15, wherein the method is a continuous method.

Aspect 17: The method of any of aspects 1 to 16, wherein the aromatic dianhydride comprises 0.1 to 3 wt %, or 0.5 to 3 wt %, or 0.5 to 2.5 wt %, or 0.5 to 2 wt %, or 0.6 to 1.6 wt %, or 0.7 to 1.3 wt %, or 0.8 to 1.2 wt % imide anhydride, based on the total weight of the aromatic dianhydride.

Aspect 18: An aromatic dianhydride made by the method of any of aspects 1 to 17, wherein the aromatic dianhydride has an imide anhydride content of 0.1 to 3 wt %, or 0.5 to 3 wt %, or 0.5 to 2.5 wt %, or 0.5 to 2 wt %, or 0.6 to 1.6 wt %, or 0.7 to 1.3 wt %, or 0.8 to 1.2 wt % imide anhydride, based on the total weight of the aromatic dianhydride.

The compositions, methods, and articles can alternatively comprise, consist of, or consist essentially of, any appropriate materials, steps, or components herein disclosed. The compositions, methods, and articles can additionally, or alternatively, be formulated so as to be devoid, or substantially free, of any materials (or species), steps, or components, that are otherwise not necessary to the achievement of the function or objectives of the compositions, methods, and articles.

All ranges disclosed herein are inclusive of the endpoints, and the endpoints are independently combinable with each other. "Combinations" is inclusive of blends, mixtures, alloys, reaction products, and the like. The terms "first," "second," and the like, do not denote any order, quantity, or importance, but rather are used to distinguish one element from another. The terms "a" and "an" and "the" do not denote a limitation of quantity, and are to be construed to cover both the singular and the plural, unless otherwise indicated herein or clearly contradicted by context. "Or" means "and/or" unless clearly stated otherwise. Reference throughout the specification to "some aspects", "an aspect", and so forth, means that a particular element described in connection with the aspect is included in at least one aspect described herein, and may or may not be present in other aspects. In addition, it is to be understood that the described elements may be combined in any suitable manner in the various aspects.

Unless specified to the contrary herein, all test standards are the most recent standard in effect as of the filing date of this application, or, if priority is claimed, the filing date of the earliest priority application in which the test standard appears.

Unless defined otherwise, technical and scientific terms used herein have the same meaning as is commonly understood by one of skill in the art to which this application belongs. All cited patents, patent applications, and other references are incorporated herein by reference in their entirety. However, if a term in the present application contradicts or conflicts with a term in the incorporated reference, the term from the present application takes precedence over the conflicting term from the incorporated reference.

Compounds are described using standard nomenclature. For example, any position not substituted by any indicated group is understood to have its valency filled by a bond as indicated, or a hydrogen atom. A dash ("-") that is not between two letters or symbols is used to indicate a point of attachment for a substituent. For example, —CHO is attached through carbon of the carbonyl group.

As used herein, the term "hydrocarbyl", whether used by itself, or as a prefix, suffix, or fragment of another term, refers to a residue that contains only carbon and hydrogen. The residue can be aliphatic or aromatic, straight-chain, cyclic, bicyclic, branched, saturated, or unsaturated. It can also contain combinations of aliphatic, aromatic, straight chain, cyclic, bicyclic, branched, saturated, and unsaturated hydrocarbon moieties. However, when the hydrocarbyl residue is described as substituted, it may, optionally, contain heteroatoms over and above the carbon and hydrogen members of the substituent residue. Thus, when specifically described as substituted, the hydrocarbyl residue can also contain one or more carbonyl groups, amino groups, hydroxyl groups, or the like, or it can contain heteroatoms within the backbone of the hydrocarbyl residue. The term "alkyl" means a branched or straight chain, unsaturated aliphatic hydrocarbon group, e.g., methyl, ethyl, n-propyl, i-propyl, n-butyl, s-butyl, t-butyl, n-pentyl, s-pentyl, and n- and s-hexyl. "Alkenyl" means a straight or branched chain, monovalent hydrocarbon group having at least one carbon-carbon double bond (e.g., ethenyl (—HC=CH$_2$)). "Alkoxy" means an alkyl group that is linked via an oxygen (i.e., alkyl-O—), for example methoxy, ethoxy, and sec-butyloxy groups. "Alkylene" means a straight or branched chain, saturated, divalent aliphatic hydrocarbon group (e.g., methylene (—CH$_2$—) or, propylene (—(CH$_2$)$_3$—)). "Cycloalkylene" means a divalent cyclic alkylene group, —C$_n$H$_{2n-x}$, wherein x is the number of hydrogens replaced by cyclization(s). "Cycloalkenyl" means a monovalent group having one or more rings and one or more carbon-carbon double bonds in the ring, wherein all ring members are carbon (e.g., cyclopentyl and cyclohexyl). "Aryl" means an aromatic hydrocarbon group containing the specified number of carbon atoms, such as phenyl, tropone, indanyl, or naphthyl. "Arylene" means a divalent aryl group. "Alkylarylene" means an arylene group substituted with an alkyl group. "Arylalkylene" means an alkylene group substituted with an aryl group (e.g., benzyl). The prefix "halo" means a group or compound including one more of a fluoro, chloro, bromo, or iodo substituent. A combination of different halo groups (e.g., bromo and fluoro), or only chloro groups can be present. The prefix "hetero" means that the compound or group includes at least one ring member that is a heteroatom (e.g., 1, 2, or 3 heteroatom(s)), wherein the heteroatom(s) is each independently N, O, S, Si, or P. "Substituted" means that the compound or group is substituted with at least one (e.g., 1, 2, 3, or 4) substituents that can each independently be a C$_{1-9}$ alkoxy, a C$_{1-9}$ haloalkoxy, a nitro (—NO$_2$), a cyano (—CN), a C$_{1-6}$ alkyl sulfonyl (—S(=O)$_2$-alkyl), a C$_{6-12}$ aryl sulfonyl (—S(=O)$_2$-aryl)a thiol (—SH), a thiocyano (—SCN), a tosyl (CH$_3$C$_6$H$_4$SO$_2$—), a C$_{3-12}$ cycloalkyl, a C$_{2-12}$ alkenyl, a C$_{5-12}$ cycloalkenyl, a C$_{6-12}$ aryl, a C$_{7-13}$ arylalkylene, a C$_{4-12}$ heterocycloalkyl, and a C$_{3-12}$ heteroaryl instead of hydrogen, provided that the substituted atom's normal valence is not exceeded. The number of carbon atoms indicated in a group is exclusive of any substituents. For example —CH$_2$CH$_2$CN is a C$_2$ alkyl group substituted with a nitrile.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

What is claimed is:

1. A method for producing an aromatic dianhydride, the method comprising
reacting an aromatic diimide with a substituted or unsubstituted phthalic anhydride in an aqueous medium in the presence of an amine exchange catalyst under conditions effective to provide an aqueous reaction mixture comprising an N-substituted phthalimide, an aromatic tetraacid salt, and at least one of an aromatic triacid salt and an aromatic imide diacid salt, wherein the reacting is at a reaction temperature that is 140 to 250° C. and a reaction pressure of 1.13 to 2.16 MPa;
removing the phthalimide from the aqueous reaction mixture by extracting the aqueous reaction mixture with an organic solvent in a single packed extraction column comprising a structured metal v-shaped packing; and
converting the aromatic tetraacid salt to the corresponding aromatic dianhydride;
wherein
the aromatic diimide is of the formula

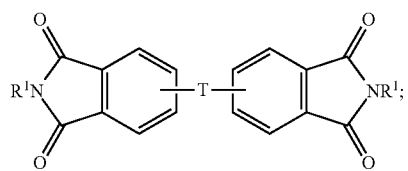

the substituted or unsubstituted phthalic anhydride is of the formula

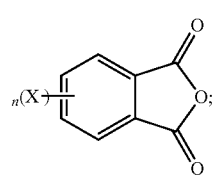

the N-substituted phthalimide is of the formula

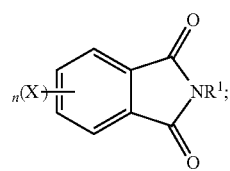

the aromatic tetraacid salt is of the formula

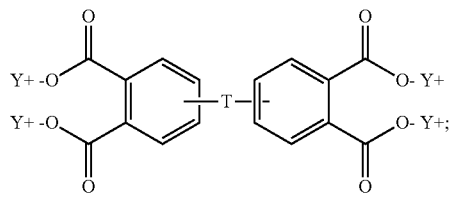

the aromatic triacid salt is of the formula

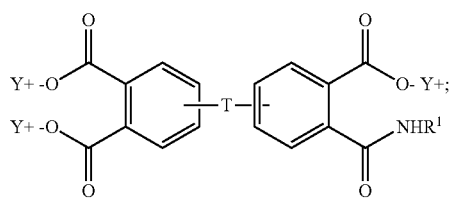

and the aromatic imide diacid salt is of the formula

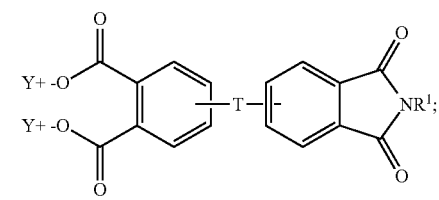

and
the aromatic dianhydride is of the formula

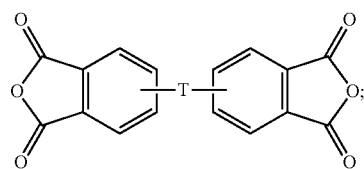

wherein in the forgoing formulas
T is —O—, —S—, —C(O)—, —SO$_2$—, —SO—, —C$_y$H$_{2y}$— wherein y is an integer from 1 to 5 or a halogenated derivative thereof or —O—Z—O—, wherein Z is an aromatic C$_{6-24}$ monocyclic or polycyclic moiety optionally substituted with 1 to 6 C$_{1-8}$ alkyl groups, 1 to 8 halogen atoms, or a combination comprising at least one of the foregoing;
R$^1$ is a monovalent C$_{1-13}$ organic group;
X is fluoro, chloro, bromo, iodo, or nitro;
n is 0 or 1; and
Y is a cationic group or a proton.

2. The method of claim 1, wherein conversion to the aromatic dianhydride is at least 75%.

3. The method of claim 1, wherein the method comprises at least one of the following process parameters:
(a) a volumetric ratio of the organic solvent to the aqueous reaction mixture of 0.5:1 to 1.5:1;
(b) an extraction column operating capacity of 8.149 to 24.47 (m$^3$/hr)/m$^2$;

(c) a dispersed phase hold up of at least 3%; and
(d) a continuous phase residence time of less than one hour.

4. The method of claim 3, wherein the method comprises process parameter (a).

5. The method of claim 3, wherein the method comprises process parameter (b).

6. The method of claim 3, wherein the method comprises process parameter (c).

7. The method of claim 3, wherein the method comprises process parameter (d).

8. The method of claim 3, wherein the method comprises at least two of the process parameters, or at least three of the process parameters, or at least four of the process parameters.

9. The method of claim 3, wherein the method comprises each of process parameters (a), (b), (c), and (d).

10. The method of claim 3, wherein the method comprises process parameters (a) and (b).

11. The method of claim 1, wherein
the substituted or unsubstituted phthalic anhydride comprises phthalic anhydride, 3-halophthalic anhydride, 4-halophthalic anhydride, 3-nitrophthalic anhydride, 4-nitrophthalic anhydride, or a combination comprising at least one of the foregoing; and
the exchange catalyst comprises a ($C_{1-20}$ alkyl)-substituted amine.

12. The method of claim 1, wherein the initial molar ratio of the substituted or unsubstituted phthalic anhydride to aromatic diimide is 4:1 to 20:1.

13. The method of claim 1, wherein the initial molar ratio of amine exchange catalyst to the substituted or unsubstituted phthalic anhydride is 1:1 to 2:1.

14. The method of claim 1, wherein
the aromatic diimide comprises 4,4'-bisphenol A-bis-N-methylphthalimide, 3,4'-bisphenol A-bis-N-methylphthalimide, 3,3'-bisphenol A-bis-N-methylphthalimide, or a combination comprising at least one of the foregoing;
the aromatic dianhydride comprises 4,4'-bisphenol A-bis-dianhydride, 3,4'-bisphenol A-bis-dianhydride, 3,3'-bisphenol A-bis-dianhydride, or a combination comprising at least one of the foregoing; and
the organic solvent comprises toluene, xylene, chlorobenzene, ortho-dichlorobenzene, or a combination comprising at least one of the foregoing.

15. The method of claim 1, wherein the removing is at an extraction temperature of 100 to 250° C.

16. The method of claim 1, wherein the method is a continuous method.

17. The method of claim 1, wherein the aromatic dianhydride comprises 0.1 to 3 wt % imide anhydride, based on the total weight of the aromatic dianhydride.

* * * * *